(12) United States Patent
Wang et al.

(10) Patent No.: US 11,210,789 B2
(45) Date of Patent: *Dec. 28, 2021

(54) DIABETIC RETINOPATHY RECOGNITION SYSTEM BASED ON FUNDUS IMAGE

(71) Applicants: SHENZHEN SIBIONICS TECHNOLOGY CO., LTD., Guangdong (CN); SHENZHEN SIBRIGHT TECHNOLOGY CO., LTD., Guangdong (CN)

(72) Inventors: Juan Wang, Guangdong (CN); Bin Xia, Guangdong (CN); Yujing Bai, Guangdong (CN); Xiaoxin Li, Guangdong (CN); Zhigang Hu, Guangdong (CN); Yu Zhao, Guangdong (CN)

(73) Assignees: Shenzhen Sibionics Technology Co., Ltd., Shenzhen (CN); Shenzhen Sibright Technology Co., Ltd., Shenzhen (CN)

( * ) Notice: Subject to any disclaimer, the term of this patent is extended or adjusted under 35 U.S.C. 154(b) by 114 days.

This patent is subject to a terminal disclaimer.

(21) Appl. No.: 16/610,771

(22) PCT Filed: Aug. 4, 2017

(86) PCT No.: PCT/CN2017/095910
§ 371 (c)(1),
(2) Date: Nov. 4, 2019

(87) PCT Pub. No.: WO2018/201633
PCT Pub. Date: Nov. 8, 2018

(65) Prior Publication Data
US 2020/0160521 A1    May 21, 2020

(30) Foreign Application Priority Data

May 4, 2017    (CN) .......................... 201710309834.4

(51) Int. Cl.
*G06T 7/00* (2017.01)
*G06K 9/42* (2006.01)
(Continued)

(52) U.S. Cl.
CPC .............. *G06T 7/0014* (2013.01); *G06K 9/42* (2013.01); *G06T 3/40* (2013.01); *G16H 50/20* (2018.01);
(Continued)

(58) Field of Classification Search
None
See application file for complete search history.

(56) References Cited

U.S. PATENT DOCUMENTS 10,413,180 B1 *   9/2019   Barriga ................... A61B 3/12
2015/0110372 A1 *   4/2015   Solanki ................. G16H 30/20
382/130

(Continued)

FOREIGN PATENT DOCUMENTS

CN        106530295 A   *   3/2017

OTHER PUBLICATIONS

M. C. Luculescu and S. Lache, "Using artificial neural networks in a Computer Aided Diagnosis system for Macular diseases," 2008 IEEE International Conference on Automation, Quality and Testing, Robotics, 2008, pp. 143-148. (Year: 2008).*

(Continued)

*Primary Examiner* — Justin P. Misleh
(74) *Attorney, Agent, or Firm* — Avant Law Group, LLC (57) ABSTRACT

Some embodiments of the disclosure provide a diabetic retinopathy recognition system (S) based on fundus image. According to an embodiment, the system includes an image acquisition apparatus (1) configured to collect fundus images. The fundus images include target fundus images and reference fundus images taken from a person. The system (Continued)

further includes an automatic recognition apparatus (2) configured to process the fundus images from the image acquisition apparatus by using a deep learning method. The automatic recognition apparatus automatically determines whether a fundus image has a lesion and outputs the diagnostic result. According to another embodiment, the diabetic retinopathy recognition system (S) utilizes a deep learning method to automatically determine the fundus images and output the diagnostic result.

9 Claims, 8 Drawing Sheets

(51) Int. Cl.
  *G06T 3/40* (2006.01)
  *G16H 50/20* (2018.01)
(52) U.S. Cl.
  CPC .............. *G06T 2207/20081* (2013.01); *G06T 2207/20084* (2013.01); *G06T 2207/30041* (2013.01); *G06T 2207/30096* (2013.01)

(56) References Cited

U.S. PATENT DOCUMENTS

| | | | | |
|---|---|---|---|---|
| 2018/0214087 A1* | 8/2018 | Balaji | .................. | A61B 3/0025 |
| 2019/0191988 A1* | 6/2019 | Gargeya | ................. | A61B 5/725 |
| 2020/0085290 A1* | 3/2020 | Wang | ................... | G06T 7/0014 |

OTHER PUBLICATIONS

J. David, R. Krishnan and S. K. A., "Neural Network Based Retinal Image Analysis," 2008 Congress on Image and Signal Processing, 2008, pp. 49-53. (Year: 2008).*

R. Priya and P. Aruna, "Automated diagnosis of Age-related macular degeneration from color retinal fundus images," 2011 3rd International Conference on Electronics Computer Technology, 2011, pp. 227-230. (Year: 2011).*

Adal, K. M., Van Etten, P. G., Martinez, J. P., Rouwen, K., Vermeer, K. A., & Van Vliet, L. J. (2017). Detection of retinal changes from illumination normalized fundus images using convolutional neural networks. In S. G. Armato, & N. A. Petrick (Eds.), Medical Imaging 2017: Computer-Aided Diagnosis (Year: 2017).*

P. Roy et al., "A novel hybrid approach for severity assessment of Diabetic Retinopathy in colour fundus images," 2017 IEEE 14th International Symposium on Biomedical Imaging (ISBI 2017), 2017, pp. 1078-1082. (Year: 2017).*

Nayak, J., Bhat, P.S., Acharya U, R. et al. Automated Identification of Diabetic Retinopathy Stages Using Digital Fundus Images. J Med Syst 32, 107-115 (2008). (Year: 2008).*

H. Pratt, F. Coenen, D.M. Broadbent, S.P. Harding, Y. Zheng Convolutional neural networks for diabetic retinopathy Procedia Comput. Sci., 90 (2016), pp. 200-205 (Year: 2016).*

* cited by examiner

FIG. 1 (a) Normal fundus

FIG. 1 (b) Fundus with lesions

FIG. 2 Diabetic retinopathy

DIABETIC RETINOPATHY RECOGNITION SYSTEM BASED ON FUNDUS IMAGE

CROSS REFERENCE TO RELATED APPLICATIONS

This application is the United States national stage entry under 35 U.S.C. 371 of PCT/CN2017/095910 filed on Aug. 4, 2017, and further claims the Chinese priority number 201710309834.4 filed on May 4, 2017, the disclosure of which are incorporated by references herein in their entireties.

FIELD OF THE DISCLOSURE

The disclosure relates generally to the field of a medical image diagnosis system. More specifically, the disclosure relates to a diabetic retinopathy recognition system based on fundus image.

BACKGROUND

In recent years, artificial intelligence technology represented by deep learning has been significantly developed, and the application thereof in the field of medical image diagnosis has also received more and more attention. Deep learning utilizes a multi-layer artificial neural network which forms more abstract high-level features by combining low level features. Deep learning can better reflect the essential characteristics of data, and the effect thereof is obviously superior to the characteristics artificially designed by expert systems. At present, extensive researches of deep learning and the like have been conducted in the field of medical imaging including pathological examination of breast cancer, lung cancer detection, cardiovascular imaging, and the like.

As is well known, medical images contain abundant details of body structure or organization. Identifying and understanding these details in medical images can help doctors and others make related diagnosis. Taking fundus images among medical images for example, a fundus image contains abundant details of vitreous body, retina, choroid, and the like. If there are related lesions, changes such as microangioma, bleeding, hard exudates, and the like can be presented in the obtained fundus image. For example, diabetic retinopathy (DR), a common fundus lesion, has become one of the main causes of blindness of the working-age adults. But if DR patients can receive early diagnosis and treatment, the visual impairment and blindness can be effectively prevented.

However, the fundus image (such as diabetic retinopathy) recognition method needs to obtain the fundus images through the fundus camera, and then requires the ophthalmologist to recognize the fundus images by eyes to make a diagnosis. Thus, it is not conductive to large-scale promotion for its large amount of work. For example, more than 50% of diabetic patients in the worldwide currently do not receive or have the opportunity to receive any form of eye exam. Therefore, in the lesion recognition of the fundus image on clinical, it is extremely urgent to provide an automatic recognition system capable of reducing the workload of the doctor and assisting the doctor in helping to complete the fundus image diagnosis.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a diabetic retinopathy recognition system based on fundus image. The system includes an image acquisition apparatus configured to collect fundus images. The fundus images include target fundus images and reference fundus images taken from a person. The system further includes an automatic recognition apparatus configured to process the fundus images from the image acquisition apparatus by using a deep learning method. The automatic recognition apparatus automatically determines whether a fundus image has a lesion and outputs the diagnostic result.

In other embodiments, the diabetic retinopathy recognition system based on fundus image involved in the disclosure utilizes deep learning method to automatically determine the fundus images and output the diagnostic result.

Optionally, the diabetic retinopathy recognition system includes an output apparatus that outputs an analysis report according to the diagnostic result.

Optionally, the image acquisition apparatus of the diabetic retinopathy recognition system is a handheld fundus camera.

Optionally, the automatic recognition apparatus of the diabetic retinopathy recognition system is arranged in a cloud server, and the image acquisition apparatus interacts with the automatic recognition apparatus based on network communication. In this case, the image acquisition apparatus interacts with the automatic recognition apparatus based on network communication.

Optionally, the automatic recognition apparatus of the diabetic retinopathy recognition system includes a pre-processing module, a first neural network, a second neural network, a feature combination module, and a third neural network. The pre-processing module is configured to separately pre-process the target fundus image and the reference fundus image. The first neural network is configured to generate a first advanced feature set from the target fundus image. The second neural network is configured to generate a second advanced feature set from the reference fundus image. The feature combination module is configured to combine the first advanced feature set and the second advanced feature set to form a feature combination set. The third neural network is configured to generate a diagnosis result of lesions according to the feature combination set. In this case, the automatic recognition apparatus simulates a diagnostic process of a doctor to make a diagnosis on the target fundus image with reference to the other fundus image of the same person.

Optionally, the target fundus image and the reference fundus image of the diabetic retinopathy recognition system are the same. In this case, even though one fundus image is used, a valid lesion diagnosis result may also be obtained.

Optionally, the target fundus image and the reference fundus image of the diabetic retinopathy recognition system are fundus images of different eyes.

Optionally, the first neural network and the second neural network of the diabetic retinopathy recognition system are the same. In this case, the number of parameters of the neural network may be controlled.

Optionally, the pre-processing module of the diabetic retinopathy recognition system includes an area detection unit, an adjustment unit, and a normalization unit. The area detection unit is configured to detect designated fundus areas in the target fundus image and the reference fundus image. The adjustment unit is configured to clip and resize the target fundus image and the reference fundus image. The normalization unit is configured to normalize the target fundus image and the reference fundus image.

Optionally, the third neural network of the diabetic retinopathy recognition system generates the diagnosis result of lesions based on the feature combination set and patient information.

BRIEF DESCRIPTION OF THE DRAWINGS

Illustrative embodiments of the disclosure are described in detail below with reference to the attached drawing figures.

FIG. 1 (a) is a schematic diagram illustrating an example of a normal-state fundus image according to the first embodiment.

FIG. 1 (b) is a schematic diagram illustrating an example of an abnormal fundus image with lesions according to the first embodiment.

DETAILED DESCRIPTION

The following describes some non-limiting exemplary embodiments of the invention with references to the accompanying drawings. The described embodiments are merely a part rather than all of the embodiments of the invention. All other embodiments obtained by a person of ordinary skill in the art based on the embodiments of the disclosure shall fall within the scope of the disclosure.

Embodiments of the disclosure are described in detail with reference to the accompanying drawings. In the following description, the same components are denoted by the same reference numerals, and the description thereof will not be repeated. In addition, the drawings are merely schematic views, and the ratio of the dimensions of the components to each other or the shape of the components may be different from the actual ones.

It should be noted that the terms "comprising" and "having", and any variants thereof, such as a process, method, system, product, or device, which are included or have a series of steps or units, are not necessarily limited to those steps or units are provided, but may include or have other steps or units not explicitly listed or inherent to such processes, methods, products or devices.

In addition, the subtitles and the like referred to in the following description of the disclosure are not intended to limit the content or scope of the disclosure, but merely serve as a hint for reading. Such a subtitle cannot be understood as content for segmenting an article, nor should the content under the subtitle be limited to the scope of the subtitle.

The disclosure relates to a diabetic retinopathy recognition system based on fundus image that may improve screening rate and accuracy. Relatively, in the disclosure, a target fundus image and a reference fundus image (which are hereinafter sometimes referred to as a "fundus image pair") are respectively used as independent input information. That is, with a reference to a "reference fundus image" of the same person for the recognition of fundus lesions in a "target fundus image", a condition of fundus lesions may be evaluated accurately and comprehensively. Here, the "target fundus image" refers to a fundus image in need of diagnosis for whether a lesion is present or what lesion is present, while the "reference fundus image" refers to a fundus image that, together with the "target fundus image", is taken from one and the same person. In the disclosure, by using a target fundus image and a reference fundus image simultaneously, an actual diagnostic process of a doctor may be simulated, which may improve the accuracy of fundus lesion diagnosis.

First Embodiment

Lesion Recognition System

Figure 1:
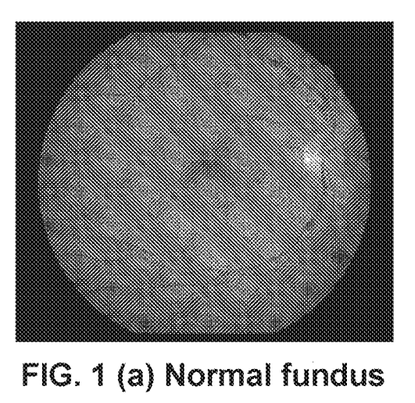
Figure 2:
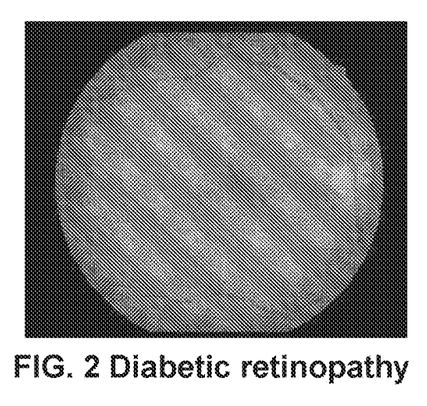
FIG. 2 is a schematic diagram illustrating examples of diabetic retinopathy fundus images with fundus lesions according to the first embodiment.

FIG. 1 (a) shows an example of a normal-state fundus image, and FIG. 1 (b) shows an example of an abnormal fundus image. FIG. 2 is a schematic diagram illustrating examples of diabetic retinopathy fundus images with fundus lesions.

The diabetic retinopathy recognition system S has the capability of determining whether a lesion is present in a fundus image. Moreover, the diabetic retinopathy recognition system S may also determine a type of lesions and to grade lesions. Common fundus lesions include diabetic retinopathy (see FIG. 2), hypertensive and arteriosclerotic fundus lesions, age-related macular degeneration fundus lesions, retinal vein occlusion fundus lesions, retinal artery occlusion fundus lesions, high myopia fundus lesions, even cardiovascular diseases and other related fundus lesions, and the like. The diabetic retinopathy recognition system S may be particularly suitable for the diabetic retinopathy of the fundus.

As mentioned above, the diabetic retinopathy recognition system may achieve unspecified categories of a disease-free diagnosis and a diagnosis of a disease existing, and may also achieve categories to be classified of no disease and a specific disease type. In addition, the categories to be classified of the diabetic retinopathy recognition system S may also be adjusted according to specific situations.

The diabetic retinopathy recognition system S may save a lot of time of a doctor on fundus screening (film reading time) and facilitate promotion and application of fundus screening, and improve screening rate, which may promote the development of health care, especially the primary health care.

Figure 3:
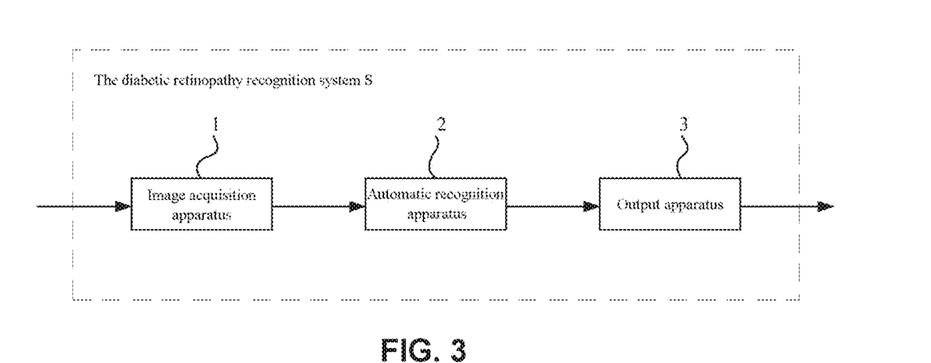
FIG. 3 is a schematic diagram showing a lesion recognition system based on fundus images according to the first embodiment.

FIG. 3 is a schematic diagram showing a lesion recognition system based on fundus images. For example, as shown in FIG. 3, the diabetic retinopathy recognition system S may be used to recognize a lesion in a fundus image. Lesions in fundus images may include, but are not limited to, diabetic retinopathy, age-related macular degeneration fundus lesions, retinal vein occlusion fundus lesions, and the like, and this embodiment may be especially well applied to the diabetic retinopathy.

The diabetic retinopathy recognition system S may include the image acquisition apparatus 1 and the automatic recognition apparatus 2. The image acquisition apparatus 1 may be used for acquiring images. The acquired images may include the target fundus image and the reference fundus image taken from the same person. In addition, the automatic recognition apparatus 2 may use deep learning method to process the fundus images from the image acquisition apparatus 1, and automatically determine whether a fundus image has a lesion and output a diagnostic result (for example, a screening report).

In addition, the image acquisition apparatus 1 is not particularly limited, as long as the apparatus is capable of acquiring fundus images. For example, a desktop fundus camera (or video camera), a handheld fundus camera (or video camera), or the like may be used. In consideration of easy operation, the image acquisition apparatus 1 may be a portable fundus camera, optionally a handheld fundus camera. In this case, the doctor or the operator or the like may conveniently acquire the fundus image (photo) of the patient.

The diabetic retinopathy recognition system S, after acquiring the fundus image of the patient, may automatically determine the fundus images and output the diagnostic result by using deep learning method, and therefore may assist the doctor in identifying lesions in the fundus images and making diagnosis, greatly improve the recognition efficiency, and may be particularly suitable for screening a wide range of fundus lesions. It is well known that deep learning is one of machine learning methods, and the learning methods thereof is based on characterization of data. In deep learning, low-level features are combined to form a more abstract high-level representation attribute category or feature as to find the distributed feature representation of data. By means of the deep learning method, the accuracy of diabetic retinopathy recognition system S may be improved.

The accuracy of the diabetic retinopathy recognition system S may be reflected by sensitivity and specificity. Specifically, screening results may include true negative, true positive, false negative and false positive. True negative refers to that a fundus image shows normal and a screening report also shows normal. True positive refers to that lesions are present in a fundus image and also shown in a screening report. False negative refers to that lesions are present in a fundus image, but a screening report shows normal. False positive refers to that a fundus image shows normal, but a screening report incorrectly displays a lesion. Thus, the sensitivity and the specificity are defined as follows.

$$\text{Sensitivity} = \frac{\text{True positives}}{\text{True positives} + \text{False negatives}} \times 100\%$$

$$\text{Specificity} = \frac{\text{True negatives}}{\text{True negatives} + \text{False positives}} \times 100\%$$

In general, the higher sensitivity and specificity are, the higher screening accuracy of the diabetic retinopathy recognition system S will be. In some screening criteria, it may be already considered as a relatively reasonable screening mode when, for example, the sensitivity is over 80% and the specificity is 90%. In contrast, the diabetic retinopathy recognition system S may have a sensitivity reaching 85% above and a specificity reaching 90% above.

In addition, the diabetic retinopathy recognition system S may also include the output apparatus 3 that outputs an analysis report according to the diagnostic result. The output apparatus 3 is not particularly limited, the output apparatus 3 may be a display screen, a terminal having a display function (for example, a tablet), a printer, or the like as long as the diagnostic result may be shown. In this case, doctors and patients may quickly understand the result of the lesion and a report that meets the required standard may be provided to the patient.

In addition, in some examples, the output apparatus 3 may be provided on the image acquisition apparatus 1. For example, the output apparatus 3 may be carried on the image acquisition apparatus 1. At this point, on the one hand, the output apparatus 3 may be provided as, for example, a display screen on the image acquisition apparatus 1; on the other hand, the output apparatus 3 may receive the processing result of the automatic recognition apparatus 2, and present the result on the output apparatus 3. In this case, the diagnostic result may be intuitively offered to the patient through the output apparatus 3 provided on the image acquisition apparatus 1, thereby facilitating on-site communication between the doctor and the patient.

In addition, the diagnosis of lesions in a fundus image may be achieved by rating. In some examples, primary rating and secondary rating may be employed. For example, a screening report provided by the automatic recognition apparatus 2 may be taken as the primary rating, and then a doctor may make secondary rating based on the screening report. Therefore, a screening result of lesions may be obtained more accurately and reliably.

In addition, the automatic recognition apparatus 2 may be arranged in a cloud server (not shown), and the image acquisition apparatus 1 interacts with the automatic recognition apparatus 2 based on network communication. In this case, the image acquisition apparatus interacts with the automatic recognition apparatus based on network communication, thereby facilitating doctors or operators or the like who is close to the side of the image acquisition apparatus to interact with the automatic recognition apparatus. Herein, the network communication may be wireless network such as Wi-Fi, a mobile communication network, or the like, or a wired network such as a wired broadband network.

In addition, the cloud server may be a self-provided network-connected server, or a part of a network-connected large server provided by the supplier. In consideration of data security, the cloud sever is optionally a self-provided network-connected server.

The automatic recognition apparatus 2 may include the artificial neural network 10A. A neural network structure employed in the artificial neural network 10A is not particularly limited. In some examples, the artificial neural network 10A may be designed as a deep neural network. For example, the first neural network 12 and the second neural network 22 described later may adopt the structure of a deep neural network. In this case, abstract image features may be extracted from a particular medical image (such as a fundus image), which may diagnose lesions like diabetic retinopathy.

Figure 4:
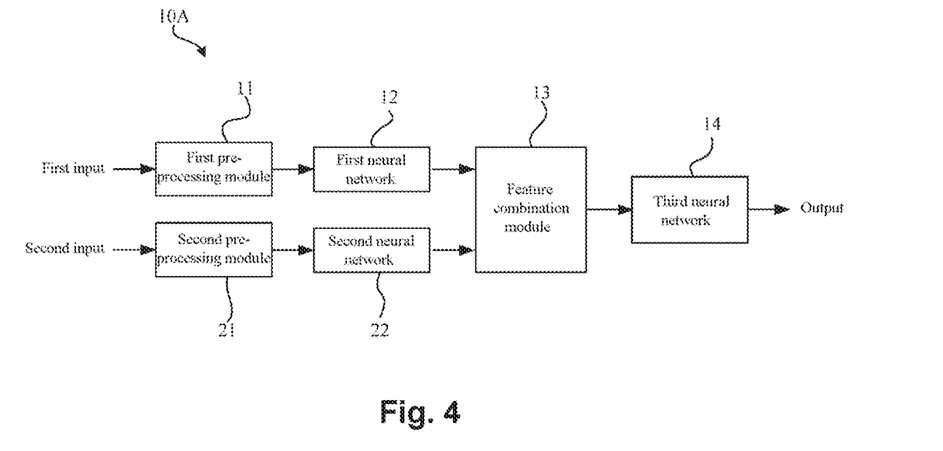
FIG. 4 is a schematic diagram showing an artificial neural network for recognizing a lesion in a fundus image according to the first embodiment.

FIG. 4 is a schematic diagram showing an artificial neural network for recognizing a lesion in a fundus image. As shown in FIG. 4, the artificial neural network 10A may include a pre-processing module, a first neural network 12, a second neural network 22, and a feature combination module 13, and a third neural network 14. Here, the pre-processing module may specifically include a first pre-processing module 11 and a second pre-processing module 21.

The pre-processing module (the first pre-processing module 11 and the second pre-processing module 21) may be configured to separately pre-process a target fundus image and a reference fundus image (a fundus image pair) that are both taken from a person. That is, the first pre-processing module 11 may pre-process the target fundus image, while the second pre-processing module 21 may pre-process the reference fundus image. In addition, the first pre-processing module 11 and the second pre-processing module 21 may be formed in one module, and may also be formed as modules independently.

As mentioned above, a target fundus image and a reference fundus image taken from the same person are used as inputs of diagnosis, that is, the target fundus image as a first input and the reference fundus image as a second input (see FIG. 4). As also mentioned above, for the diagnosis of fundus lesions in a target image, besides the target fundus image itself, a reference fundus image is used as a diagnostic reference. This process stimulates an actual situation where a doctor will make a comparison with and a reference to a plurality of fundus images at the same time in an actual diagnosis, and therefore, the diagnosis accuracy of lesions in a fundus image may be improved.

In addition, in the artificial neural network 10A, the inventors of the disclosure also take the following facts into account. 1) The same diagnosis result required be obtained for different images (including a target fundus image and a reference fundus image) taken from the same eye. 2) Statistically, fundus lesions of the left and the right eye of a person (patient) are similar. Therefore, when making a diagnosis on a target fundus image, the diagnosis accuracy may be improved by using another fundus image from the same patient as assist.

In addition, during the training or testing process of the artificial neural network 10A, two fundus images taken from a single eye (the left or right eye) of a person may be used in some examples. In this case, any one of the two fundus images may be used as the target fundus image and the other as the reference fundus image. In other examples, two fundus images respectively belongs to two eyes of a person may also be used. Similarly, in this case, any one of the two fundus images may be used as the target fundus image and the other as the reference fundus image.

In addition, in the artificial neural network 10A, in some examples, a target fundus image and a reference fundus image may be the same (that is, a first input and a second input may be the same). In this case, even though only one fundus image taken from a patient is used by the artificial neural network 10A during the training or testing process, this fundus image (for example, by copying into two fundus images) may be used as the target fundus image and the reference target fundus separately. Thus, a valid lesion diagnosis result may also be obtained.

In addition, four fundus images, including two fundus images taken from a left eye and two fundus images taken from a right eye, may also be used. In this case, any one of the four fundus images may be used as the target fundus images and the others as the reference fundus images.

In addition, in some examples, a plurality of fundus images (for example, more than five) may be obtained during acquiring fundus image by the image acquisition apparatus. In this case, any one of the plurality of fundus images may be used as the target fundus images and the others as the reference fundus images. In other examples, numerically equal fundus images taken from left and right eyes may further be used.

In addition, fundus images (including target fundus images or reference fundus images) used in this embodiment are not particularly limited and the fundus images may be color images (such as RGB images), and may also be gray images.

In the present embodiment, a fundus image pair consisting of a target fundus image and a reference fundus image is used as inputs (including a first input and a second input). In this case, since the target fundus image and the reference fundus image (the fundus image pair) are similar or are same images, therefore, the subsequent screening capability of the artificial neural network may be improved by putting the target fundus image and the reference fundus image separately in a first neural network and a second neural network (that is, the target fundus image is used as the first input in the first neural network, and the reference fundus image as the second input in the second neural network, as shown in FIG. 4) to extract features of the fundus images.

In addition, in the artificial neural network 10A, a target fundus image and a reference fundus image may be fundus images of different eyes respectively. In this case, it may be conductive to improve the trained artificial neural network 10A so that the trained artificial neural network 10A may be closer to true diagnosis situations.

Pre-Processing Module

Figure 5:
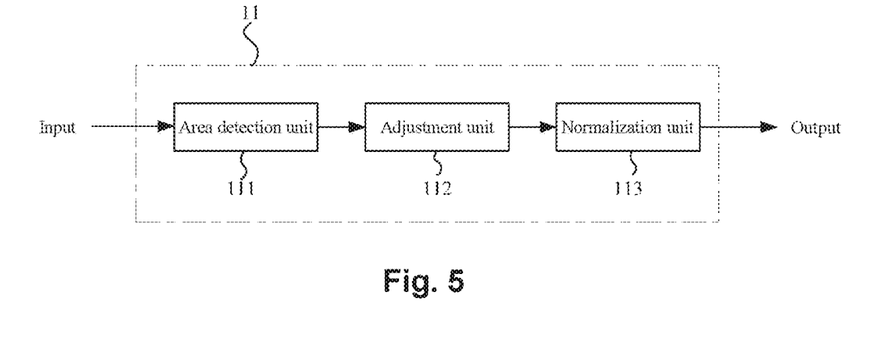
FIG. 5 is a schematic diagram showing the pre-processing module of the artificial neural network according to the first embodiment.

FIG. 5 is a schematic diagram of a pre-processing module of the artificial neural network 10A.

As mentioned above, the pre-processing module (including a first pre-processing module 11 and a second pre-processing module 21) may be configured to separately pre-process a target fundus image and a reference fundus image (a fundus image pair) that are both taken from a person. In particular, the first pre-processing module 11 and the second pre-processing module 21 may perform pre-processing such as fundus area detection, image clipping, resizing, normalizing, and the like, for fundus images. That is, the first pre-processing module 11 may perform fundus area detection, image clipping, resizing, normalizing, and the like for the target fundus image, and the second pre-processing module 21 may perform fundus area detection, image clipping, resizing, normalizing, and the like for the reference fundus image.

Since the first pre-processing module 11 and the second pre-processing module 21 may be set as the same module, therefore, the first pre-processing module 11 will be described below in detail, and the second pre-processing module 12 may be completely the same in structure with the first pre-processing module 11.

As shown in FIG. 5, the first pre-processing module 11 of the artificial neural network 10A mainly includes an area detection unit 111, an adjustment unit 112 and a normalization unit 113.

In the first pre-processing module 11, the area detection unit 111 may detect fundus areas from various fundus images. A fundus area to be detected may be, for example, a fundus area centered on an optic disk, or a fundus area including an optic disk and centered on a macula, or the like. Any area, whether centered on an optic disk or including the optic disk and centered on a macula, may show fundus lesions effectively. In some examples, the area detection unit 111 may detect a specific area in a fundus image by, for example, a sampling threshold method or Hough transform for later use by the artificial neural network. For example, referring to the fundus images shown in FIG. 1 (*a*) and FIG. 1 (*b*) and the like, the brightest circle in any fundus image is the optic disk, and the darkest area is the macula or retina fovea, together with blood vessels leading out from the optic disk.

In addition, as shown in FIG. 5, the adjustment unit 112 may be configured to clip and resize a fundus image (a target fundus image). Due to different sizes of the human eyes and different fundus camera devices used, the obtained fundus images may vary in resolution, fundus area size and the like. Therefore, it is necessary to resize such fundus images. For example, with the adjustment unit 112, a fundus image may be clipped according to a specific specification. In some examples, a square fundus image may be obtained by clipping. Moreover, a fundus image is not limited to square, and may also be, for example, rectangular, round, oval, and the like. Further, the adjustment unit 112 may also perform other processing on a fundus image including, for example, distinguishing a fundus area from a patient information area in a fundus image (e.g., some fundus images may include names, medical insurance numbers, and the like), and resizing fundus images processed by different fundus camera devices using different algorithms to solve problems such as uniformizing fundus background.

In addition, in some examples, the adjustment unit 112 may resize a fundus image to a specified size (e.g., pixel size), such as 256×256, 512×512, 1024×1024 pixels, and the like. However, this embodiment is not limited thereto, and depending on particular requirements, the size of a fundus image may also be a size (pixel size) of any other specification, such as 128×128, 768×768, 2048×2048 pixels, and the like.

Although there are no limitations to the size of a fundus image, considering more accurately recognizing more details of a fundus image, the size of a fundus image may be optionally higher than or equal to 512×512 pixels. The deep learning framework Inception-v3 involved in the patent document 1 as mentioned above uses an image of only 299×299 pixels. However, since the feature of many fundus diseases (such as the features of early lesions of the diabetic retinopathy) may not obviously shown at such a pixel level, in this case, it may result in loss of important image detail information, for example, loss of low-grade fundus lesion (such as first-grade diabetic retinopathy) information during a subsequent down-sampling process (especially in large-scales down-sampling). Based on this, in the patent document 1, the first-grade diabetic retinopathy is treated as a healthy eye, which may thus lead to insufficient diagnosis of lesions in a fundus image and poor clinical effect. In contrast, by limiting the size of a fundus image as described above, the loss of detail information of a fundus image may be effectively inhibited and thus improving diagnosis accuracy of fundus lesions.

In addition, in the first pre-processing module 11, the normalization unit 113 may be configured to normalize a fundus image (a target fundus image). Due to the difference in the fundus between different races and fundus imaging devices or conditions, fundus images may greatly vary, and therefore, it is necessary to perform normalization processing on the images.

The normalization way of the normalization unit 113 is not particularly limited. For example, a zero mean, a unit standard deviation, and the like may be adopted for normalization. In addition, in some examples, the normalization may be within of range of [0, 1]. By normalization, the difference of different fundus images may be overcome and the performance of the artificial neural network may be improved.

Figure 6:
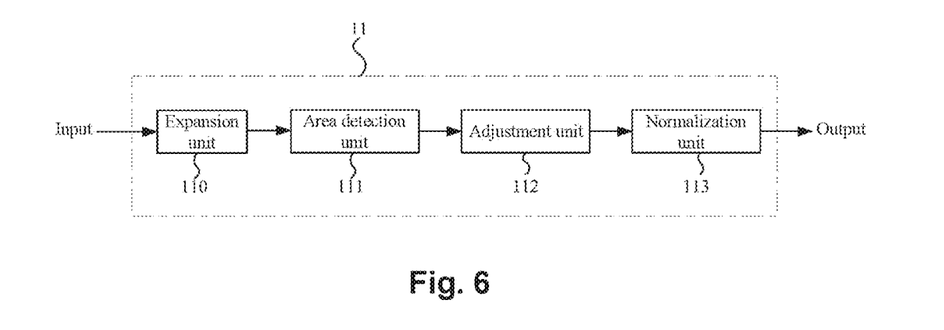
FIG. 6 is a schematic diagram showing a variation of the pre-processing module in FIG. 5.

FIG. 6 is a schematic diagram showing a variation of the pre-processing module 11. As shown in FIG. 6, the first pre-processing module 11 may also have an expansion unit 110. The expansion unit 110 may be disposed ahead of the area detection unit 111, which is not limited thereto in this embodiment.

The expansion unit 110 may be configured for data expansion on a fundus image at the training phase of the neural network. With the expansion unit 110, data expansion may be performed on an obtained fundus image (a target fundus image) to increase a sample size of fundus images, which may overcome the over-fitting problem and improve the performance of the artificial neural network. In addition, what needs to be noted is that the expansion unit 110 is generally limited to expand data samples at the training phase of the neural network as described later and may not be used at the testing phase of the neural network.

In addition, there are no particular limitations to the expansion way taken by the expansion unit 110. For example, in some examples, sample expansion may be achieved through various image transformation of a fundus image. Such image transformation ways may include symmetric transformation, inverse transformation, rotation transformation, pixel translation, and the like, and may also include adjustment of contrast, brightness, color, sharpness, and the like of an image.

The configuration and functionality of the first pre-processing module 11 have been described above, and similarly, the second pre-processing module 21 may also have the same configuration and functionality with the first pre-processing module 11. In this case, a reference fundus image as a second input may be effectively pre-processed through the second pre-processing module 21, so that the artificial neural network (the second neural network and the third neural network) may process the reference fundus image subsequently.

As mentioned above, a target fundus image and a reference fundus image may be effectively pre-processed, respectively, by means of the first pre-processing module 11 and the second pre-processing module 21, thereby facilitating subsequent further processing (such as feature extraction and the like) on fundus images by each neural network.

First/Second Neural Network

The first neural network 12 may be configured to generate a first advanced feature set from a pre-processed target fundus image. Similarly, the second neural network 22 may be configured to generate a second advanced feature set from a pre-processed reference fundus image. The first neural network and the second neural network may achieve abstract description of the target fundus image and the reference fundus by, for example, combining a plurality of layers of low-level features (pixel-level features). Here, the advanced features are merely relative to primary features (e.g., pixel-level features) of an original image after being processed by the artificial neural network, and not intended to precisely describe that such features are advanced. However, in general, after being processed by the neutral network, a tendency of being more high-level and abstract will be shown as the layer of the neutral network gets deeper. In addition, a feature set generally refers to including two or more than two features, and may sometimes be referred to as a "feature matrix" in the disclosure. Moreover, in some special cases, a feature set may also have only one feature, for example, an intermediate result, and then a "feature set" may refer in particular to a single "feature".

In addition, the first neural network 12 and the second neural network 22 may both be designed as a convolutional neural network (CNN). Due to the advantages of weight-sharing, local receptive field, and the like of the convolutional neural network, training of parameters may be greatly reduced, and may therefore increase processing speed and save hardware overhead. Additionally, the convolutional neural network may perform image recognition more effectively.

Figure 7:
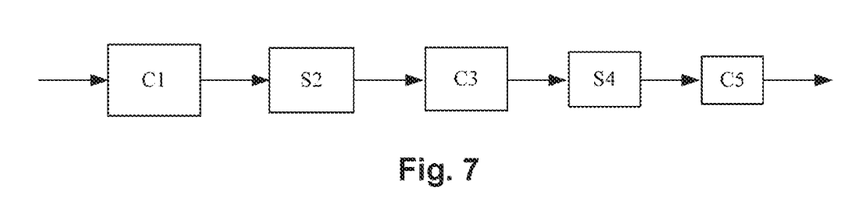
FIG. 7 is a schematic diagram showing a network structure example of the artificial neural network according to the first embodiment.
Figure 8:
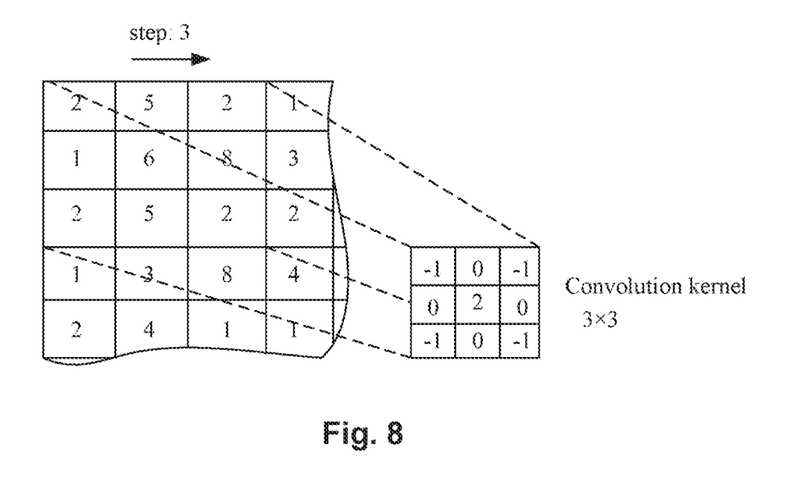
FIG. 8 is a schematic diagram showing an example of a convolution kernel employed in the artificial neural network in FIG. 7.

FIG. 7 is a schematic diagram showing a network structure example of the artificial neural network. FIG. 8 is a schematic diagram showing an example of a convolution kernel employed in the artificial neural network in FIG. 7.

In some examples, convolutional neural networks may be used as the first the neural network 12 and the second neural network 22 respectively. For example, the network structures of the first neural network 12 and the second neural network 22 may be designed as neural network structures as shown in FIG. 6 and FIG. 7. The network structures may be simplified in the following representation.

-C1-S1-C2-S2-C3-S3-C4-

Here, C (including C1, C2, C3, and C4) represents a convolution layer, and S (including S1, S2, and S3) represents a pooling layer (sometimes referred to as a "down-sampling layer"). In some examples, except layer C1 that uses a 5×5 convolution kernel, each of the other convolution layers may use a 3×3 convolution kernel. In this case, for a medical image (a fundus image) of a specified size, such as 256×256 and 512×512 pixels, increase of training parameters may be greatly inhibited, and the training efficiency may be improved.

In addition, in the above convolutional neural network, the way of pooling may be max-pooling, mean-pooling, stochastic-pooling, and the like. With the pooling operation, on one hand, reduced dimensionality and improved operation efficiency may be achieved. Additionally, the neural network may be enabled to extract more abstract high-level features, which may improve the diagnosis accuracy of fundus lesions.

In addition, in the above convolutional neural network, the number of convolution layers and the number of pooling layers may also be increased correspondingly according to the situation. In this case, the neural network may also be enabled to extract more abstract high-level features to further improve the diagnosis accuracy of fundus lesions.

In addition, in the artificial neural network 10A, the first neural network 12, and the second neural network 22 may be completely the same. Specifically, the network structure of the first neural network 12 and the network structure of the second neural network 22 may be completely the same. In this case, the number of parameters of the artificial neural network may be reduced, which may inhibit over-fitting of the neural network.

In addition, the convolutional neural network structure used for the first neural network 12 and the second neural network 22 is not limited thereto, and other convolutional neural network structures may also be adopted as long as advanced features may be extracted from original fundus images (a target fundus image and a reference fundus image). Moreover, it is noted that the first neural network 12 and the second neural network 22 are mainly intended for feature extraction and not for directly outputting a lesion diagnosis result.

Feature Combination Module

As shown in FIG. 4, the feature combination module 13 may be configured to combine a first advanced feature set generated by the first neural network 12 and a second advanced feature set generated by the second neural network 22 to form a feature combination set. Here, the "feature set" may refer to a "feature sequence", a "feature vector", a "feature value set", and the like, and the meaning thereof should be understood in the broadest manner.

In some examples, the feature combination module 13 may combine a first advanced feature set and a second advanced feature set to form a one-dimensional feature vector (a feature combination set). In addition, in other examples, the feature combination module 13 may also calculate differences between a first advanced feature set and a second advanced feature set to obtain a feature combination set. Further, in other examples, the feature combination module 13 may also calculate mean values of a first advanced feature set and a second advanced feature set to obtain a feature combination set. Further, in other examples, the feature combination module 13 may perform linear or nonlinear transformation on a first advanced feature set and a second advanced feature set to obtain a feature combination set and the like.

The features generated from the first neural network 12 and the features generated from the second neural network 22 may be combined by the feature combination module 13, thereby facilitating subsequent processing by the third neural network 14.

Third Neural Network

The third neural network 14 may be configured to generate a diagnosis result of lesions according to the result of feature combination (a feature combination set). As shown in FIG. 4, the third neural network 14 may produce a diagnosis result on the input target fundus image based on a result obtained by the feature combination module 13. That is, the third neural network 14 generates a diagnosis result of lesions according to a feature combination set.

The output dimensions of the third neural network 14 are consistent with categories to be classified (e.g., a lesion type). That is, for example, when the categories to be classified are a disease-free category and a disease existing category, the output dimensions of the third neural network 14 may be 2; and if the categories to be classified are a disease-free category and specific symptoms (e.g., 5 symptoms), the output dimensions of the third neural network 14 may be 6. In addition, the output dimensions of the third neural network 14 may be adjusted according to the actual situation.

In some examples, the outputs of the third neural network 14 may be values (percentages) between 0 and 1, and such values may each be interpreted as a probability that a target fundus image is classified into a particular category (lesion type). Then, the sum of the outputs of the third neural network 14 is 1 (probability sum).

Nn output probability of the third neural network 14 is used for achieving final diagnoses. In some examples, when the probability of a particular category is the highest, it is determined that the fundus has lesions of the corresponding category. For example, if the probability of no lesion among all categories to be classified is the highest, the target fundus image is determined to be lesion-free. If the probability of diabetic retinopathy is the highest, the target fundus image is then determined to be diabetic retinopathy.

In addition, the network structure of the third neural network 14 is not particular limited. In some examples, the third neural network 14 may use a convolution layer, a fully connected layer and other auxiliary layers (such as a batch normalization layer, a pooling layer, and the like). For example, in some cases, the output layers of the third neural network 14 may include a single convolution layer, two fully connected layers and an output layer (softmax layer). Moreover, in other cases, the output layers of the third neural network 14 may also adopt two convolution layers, two pooling layers, three fully connected layers, and an output layer (e.g., a softmax layer).

As mentioned above, by using a target fundus image and a reference fundus image as independent input information respectively, extraction of advanced features from the target fundus image by the first neural network and extraction of advanced features from the reference fundus image by the second neural network may be facilitated. Furthermore, the advanced features that are obtained from the first neural network and the second neural network, respectively, are combined and then a diagnosis result of lesions is obtained by the third neural network. Thus, the diagnostic performance of lesions in a fundus image may be significantly improved.

Training and Testing

The first neural network 12, the second neural network 22 and the third neural network 14 may be trained together to obtain an optimal neural network structure. For example, where convolutional neural networks are used as a first neural network 12 and a second neural network 22, when the above described neural networks are trained, the convolutional neural networks may be trained by using a fundus image pair (including a target fundus image and a reference fundus image) of the training set.

Moreover, as described, the first neural network 12, the second neural network 22, and the third neural network 14 may be trained together, but the embodiment is not limited thereto. For example, the first neural network 12 and the second neural network 22 may be trained first by the way of training an auto-encoder network and then be trained together with the third neural network 14.

In addition, for the fundus images, during the training or testing process of the artificial neural network 10A, two fundus images of a single eye from a person may be used, and two fundus images of two eyes from a person may also be used.

Furthermore, during the training or testing process of the artificial neural network 10A, four fundus images including two fundus images taken from the left eyes and two fundus images taken from the right eye may also be used. In this case, it may better match the actual situation of diagnosis of lesions in a fundus image. Incidentally, the international popular gold standard for diagnosis of lesions in fundus images at present is using seven fundus images of different fundus areas and having a visual angle of 30 degrees. However, the inventors of the disclosure have found in long-term practice that an equivalent lesion diagnosis effect may also be achieved by using, for example, four fundus images from two eyes which have specified areas and a visual angle of 45 degrees.

Additionally, this embodiment is not limited thereto, and more fundus images taken from two eyes of a person may also be used. Optionally, numerically equal fundus images taken from left and right eyes are used.

During the training process of the artificial neural network 10A, 50-200 thousand fundus images from a cooperative hospital and having patient information removed are selected as a training set, for example, 5000-20000 fundus images as a testing set. During the training or testing process, the fundus images are unified to RGB color fundus images in a size of, for example, 512×512 or 1024×1024 pixels.

During the training process, parameters are adjusted by using the stochastic gradient descent method, thereby obtaining a final training result. Then, the trained artificial neural network 10A is employed to recognize fundus images in the testing set, obtaining an average recognition accuracy of, for example, 90% and above. It thus may be seen that the artificial neural network 10A may obtain an improved lesion diagnosis accuracy with consideration of the fundus clinical circumstance.

Lesion Recognition Process

Figure 9:
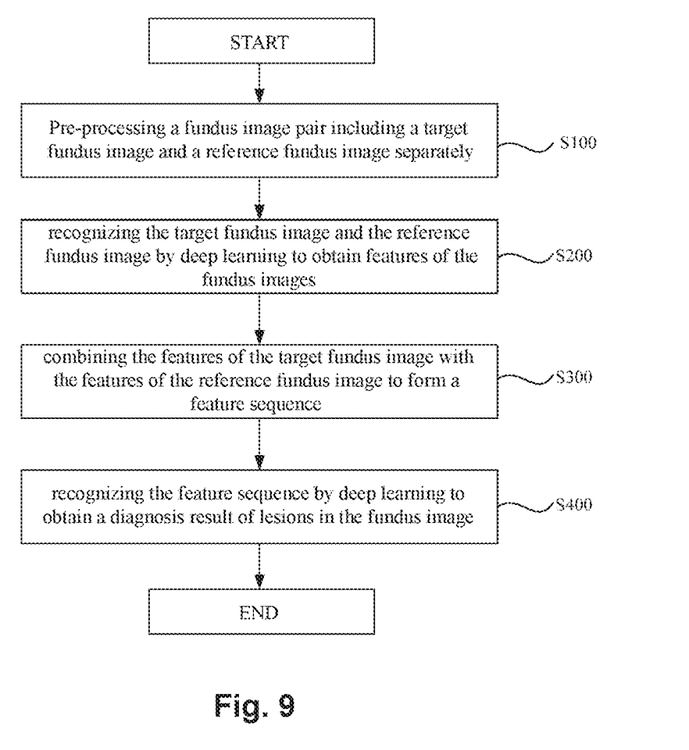
FIG. 9 is a flowchart showing a method for recognizing a lesion in a fundus image by the artificial neural network according to the first embodiment.

FIG. 9 is a flowchart showing a method for recognizing a lesion in a fundus image using the artificial neural network 10A. Hereinafter, with reference to FIG. 9, the method for recognizing a lesion in a fundus image using the artificial neural network 10A will be described below in detail.

In the method for recognizing a lesion in a fundus image, first, separately pre-processing is performed on a fundus image pair including a target fundus image and a reference fundus image (step S100) to obtain fundus images satisfying specified conditions.

In step S100, for example, area detection, image clipping, resizing, normalization, and the like may be performed on the fundus image. In addition, in step S100, data expansion may also be performed on the fundus image pair (including the target fundus image and the reference fundus image) during neural network training to increase the size of data samples for training, which may improve the accuracy of diagnosis of fundus lesions. In some examples, the target fundus image and the reference fundus image may be the same image.

Then, after the step S100, respective operations may be performed on the target fundus image and the reference fundus image by using the deep learning method so as to obtain the features of the target fundus image and the features of the reference fundus image (step S200). In step S200, advanced features of the target fundus image and advanced features of the reference fundus image may be obtained by means of, for example, convolutional neural network. Since the convolutional neural network has the advantages of local receptive field and weight-sharing and is conducive to extraction of advanced features of a fundus image, the operation efficiency may be improved and the hardware overhead may be saved.

After step S200, the features of the target fundus image and the features of the reference fundus image may be combined to form a feature combination set (step S300). As described above, forming a feature combination set is beneficial for the synthesis of the features of the target fundus image and the features of the reference fundus image, thereby facilitating subsequent classification and diagnosis.

Finally, the feature combination set may be recognized by using a deep learning method so as to obtain a diagnosis result of lesions in the fundus image (step S400). In step S400, the diagnosis result of fundus lesions may be obtained by using, for example, an average operator, a maximum operator, logistic regression, random forest, a support vector machine (SVM), and the like.

Second Embodiment

Figure 10:
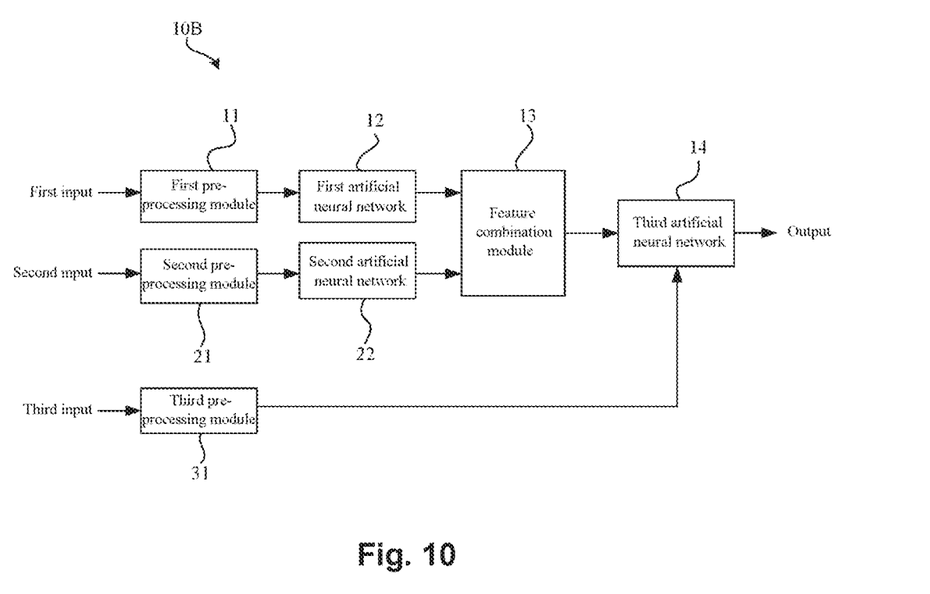
FIG. 10 is a schematic diagram showing an artificial neural network according to the second embodiment.
Figure 11:
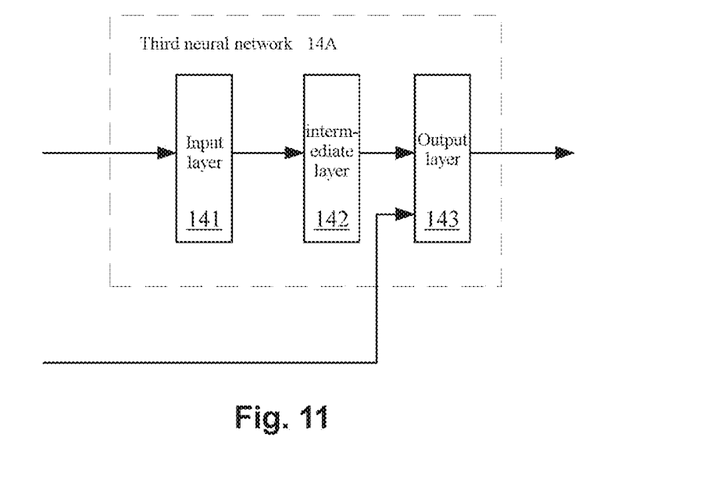
FIG. 11 is a schematic diagram illustrating an example of a third neural network according to the second embodiment.
Figure 12:
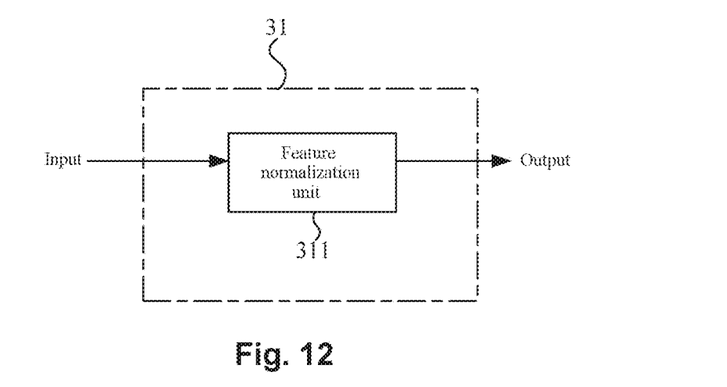
FIG. 12 is a schematic diagram showing a pre-processing module of the artificial neural network according to the second embodiment.

FIG. 10 is a schematic diagram showing an artificial neural network 10B according to the second embodiment of the disclosure. FIG. 11 is a diagram illustrating an example of a third neural network 14 according to the second embodiment of the disclosure. FIG. 12 is a schematic diagram showing a third pre-processing module 31 of the artificial neural network 10B according to the second embodiment of the disclosure.

The difference between the artificial neural network 10B and the artificial neural network 10A is that the artificial neural network 10B includes the third pre-processing module 31, and the third neural network 14 may generate a diagnosis result of lesions according to the above feature combination set and patient information (see FIG. 10). The artificial neural network 10B may also improve the accuracy (including sensitivity and specificity) of screening of fundus lesions.

The feature combination set has been described in detail in the first embodiment, and thus will not be redundantly described herein. In this embodiment, the feature combination set obtained by the feature combination module 13 is input into the third neural network 14. Further, the third neural network 14 generates a diagnosis result of lesions according to the feature combination set and patient information.

The output dimensions of the third neural network 14 are consistent with categories to be classified (e.g., a lesion type). That is, for example, when the categories to be classified are a disease-free category and a disease existing category, the output dimensions of the third neural network 14 may be 2; and if the categories to be classified are disease-free and specific symptoms (e.g., 5 symptoms), the output dimensions of the third neural network 14 may be 6. In addition, the output dimensions of the third neural network 14 may be adjusted according to the actual situation.

In some examples, the outputs of the third neural network 14 may be values (percentages) between 0 and 1, and such values may each be interpreted as a probability that a target fundus image is classified into a particular category (lesion type). Then, the sum of the outputs of the third neural network 14 is 1 (probability sum).

An output probability of the third neural network 14 is used for achieving final diagnoses. In some examples, when the probability of a particular category is the highest, it is determined that the fundus has lesions of the corresponding category. For example, if the probability of no lesion among all categories to be classified is the highest, the target fundus image is determined to be lesion-free. If the probability of diabetic retinopathy is the highest, the target fundus image is determined to be diabetic retinopathy.

In addition, in some examples, the patient information includes at least one of a patient's visual acuity, age, gender, and past medical history. Moreover, the patient information may also include body weight. According to the findings of the inventors of the disclosure in years of ophthalmic practice, a patient's visual acuity, age, gender, past medical history, body weight, and the like are all closely related to fundus lesions. That is, factors such as a patient's visual acuity, age, gender, past medical history, and the like are also important reference factors for fundus lesion diagnosis.

Furthermore, the artificial neural network 10B may include a third pre-processing module 31 by which the patient information may be pre-processed. The third pre-processing module 31 may include a feature normalization unit 311 by which, for example, the values included in the patient information may be normalized to an interval of [0, 1], which may avoid possible adverse effects of the patient information on subsequent processing by the neural network.

Patient information is added to the artificial neural network 10B and provided as a third input to the third neural network 14A so as to improve the lesion recognition capability of the artificial neural network 10B. In the third neural network 14, apart from the features output by the feature combination module 13 used as inputs to the third neural network 14, patient information is output as features to the third neural network 14. Therefore, the third neural network 14 may generate a diagnosis result of lesions according to the feature combination set and the patient information.

In addition, the network structure of the third neural network 14 is not particularly limited. In some examples, the third neural network 14 may be implemented by using various combinations of a convolution layer, a fully connected layer and other auxiliary layers (such as a batch normalization layer, a pooling layer, and the like). For example, in some cases, the output layers of the third neural network 14 may include a single convolution layer, two fully connected layers and an output layer (e.g., softmax layer). Moreover, in other cases, the output layers of the third neural network 14 may also include two convolution layers, two pooling layers, three fully connected layers, and an output layer like softmax layer (see FIG. 11).

Furthermore, the third neural network 14 may include a fully connected layer, and patient information is used as inputs to the fully connected layer. In particular, for example, when the third neural network 14 has a neural network structure of a convolution layer, a pooling layer and a fully connected layer, patient information may be used as inputs to the fully connected layer (see FIG. 11). When the third neural network 14 has a plurality of fully connected layers, patient information may be used as inputs to a first fully connected layer, and may also be used as inputs to any other fully connected layer. In this case, the artificial neural network 10B performs diagnosis in combination with both fundus image information (feature combination information) and patient information, which is closer to the actual clinical diagnostic process of a doctor, and therefore, the accuracy of recognition of lesions in a fundus image may be improved.

Some embodiments of the disclosure may have one or more of the following effects. The disclosure may provide a diabetic retinopathy recognition system based on fundus image which may improve screening rate and accuracy. The disclosed system may utilize deep learning method to automatically determine the fundus images and output the diagnostic result. The disclosed system may assist the doctor in identifying lesions in the fundus images and making diagnosis. The disclosed system may greatly improve the recognition efficiency and be particularly suitable for screening a wide range of fundus lesions. The diabetic retinopathy recognition system may help doctors and patients quickly understand the result of the lesion and a report that meets the required standard may be provided to the patient. The diabetic retinopathy recognition system may help doctors or operators conveniently acquire fundus images (photos) of patients. The diabetic retinopathy recognition system may help to facilitate doctors or operators or the like who is close to the side of the image acquisition apparatus to interact with the automatic recognition apparatus. The automatic recognition apparatus may simulate a diagnostic process of a doctor to make a diagnosis on the target fundus image with reference to the other fundus image of the same person, which may improve the diagnosis accuracy of lesions in the fundus image. The number of parameters of the neural network may be controlled, which may improve the training efficiency of the neural network and facilitating to inhibit overfitting. The target fundus image and the reference fundus image may be effectively pre-processed and the accuracy of subsequent extraction of image features by each neural network may be improved, thus improving the diagnosis result of lesions in the fundus image. The third neural network of the diabetic retinopathy recognition system may generate the diagnosis result of lesions based on the feature combination set and patient information. Therefore, it may be closer to an actual diagnostic process of a doctor so that the accuracy of diagnosis may be improved.

It should be noted that while different method examples as mentioned before are described as a combination of a series of operations for the sake of simple description, those skilled in the art will understand that the present invention is not limited to the described sequence of operations because some steps may be performed in other sequences or simultaneously according to the present application.

In the above embodiments or examples, the description of each embodiment or example has a focus, and the parts that are not described in detail in a certain embodiment or example may refer to related descriptions of other embodiments or examples.

In addition, the method steps according to the present invention may be sequentially adjusted, merged, and deleted according to actual needs. Units or subunits in the apparatus according to the present invention may be merged, divided, and deleted according to actual needs.

One of ordinary skill in the art can understand that all or part of the steps in the above embodiments can be completed by a program to instruct related hardware, and the program can be stored in a computer readable storage medium. The storage medium includes Read-Only Memory (ROM), Random Access Memory (RAM), Programmable Read-only Memory (PROM), and Erasable Programmable Read Only Memory (EPROM), One-time Programmable Read-Only Memory (OTPROM), Electrically-Erasable Programmable Read-Only Memory (EEPROM), Compact Disc Read-Only Memory (CD-ROM) or other optical disc storage, disk storage, magnetic tape storage, or any other medium readable by a computer that may be used to carry or store data.

While the present invention is described above in detail in combination with the drawings and embodiments, it will be understood that the above descriptions do not limit the invention in any form. The present invention may be modified and changed as needed by those skilled in the art without departing from the spirit and scope of the invention, and such modifications and variations are within the scope of the invention.

Many different arrangements of the various components depicted, as well as components not shown, are possible without departing from the spirit and scope of the disclosure. Embodiments of the disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A diabetic retinopathy recognition system, comprising:
    an image acquisition apparatus configured to collect fundus images, the fundus images comprise target fundus images and reference fundus images taken from a person; and
    an automatic recognition apparatus configured to process the fundus images from the image acquisition apparatus by using a deep learning method, and automatically determine whether a fundus image has a lesion and output a diagnostic result;
    wherein the automatic recognition apparatus comprises:
        a pre-processing module configured to separately pre-process the target fundus images and the reference fundus images;
        a first neural network configured to generate a first advanced feature set from the target fundus images;
        a second neural network configured to generate a second advanced feature set from the reference fundus images;
        a feature combination module configured to combine the first advanced feature set and the second advanced feature set to form a feature combination set; and
        a third neural network configured to generate a diagnosis result of lesions according to the feature combination set.

2. The diabetic retinopathy recognition system of claim 1, further comprising an output apparatus that outputs an analysis report according to the diagnostic result.

3. The diabetic retinopathy recognition system of claim 1, wherein the image acquisition apparatus is a handheld fundus camera.

4. The diabetic retinopathy recognition system of claim 1, wherein the automatic recognition apparatus is arranged in a cloud server, and the image acquisition apparatus interacts with the automatic recognition apparatus based on network communication.

5. The diabetic retinopathy recognition system of claim 1, wherein the target fundus images, and the reference fundus images are the same.

6. The diabetic retinopathy recognition system of claim 1, wherein the target fundus images and the reference fundus images are fundus images of different eyes.

7. The diabetic retinopathy recognition system of claim 1, wherein the first neural network and the second neural network are the same.

8. The diabetic retinopathy recognition system of claim 1, wherein the pre-processing module comprises:
    an area detection unit configured to detect designated fundus areas in the target fundus images and the reference fundus images;
    an adjustment unit configured to clip and resize the target fundus images and the reference fundus images; and
    a normalization unit, configured to normalize the target fundus images and the reference fundus images.

9. The diabetic retinopathy recognition system of claim 1, wherein the third neural network generates the diagnosis result of lesions based on the feature combination set and patient information.

* * * * *